United States Patent [19]

Moggi et al.

[11] 4,065,469

[45] Dec. 27, 1977

[54] PROCESS FOR THE SYNTHESIS OF DIBENZOFURAN

[75] Inventors: Pietro Antonio Moggi, Milan; Giuseppe Iori, San Donato Milanese (Milan), both of Italy

[73] Assignee: ANIC, S.p.A., Palermo, Italy

[21] Appl. No.: 635,235

[22] Filed: Nov. 25, 1975

[30] Foreign Application Priority Data

Nov. 25, 1974 Italy .................................. 29771/74

[51] Int. Cl.$^2$ .......................................... C07D 307/91
[52] U.S. Cl. ................................................ 260/346.71
[58] Field of Search ................................. 260/346.2 M

[56] References Cited

U.S. PATENT DOCUMENTS 3,228,966  1/1966  Adams ........................... 260/346.1 R

FOREIGN PATENT DOCUMENTS 1,007,772  5/1957  Germany.
690,486  6/1965  Italy.
769,558  6/1967  Italy.

*Primary Examiner*—Henry R. Jiles
*Assistant Examiner*—Bernard Dentz
*Attorney, Agent, or Firm*—Morgan, Finnegan, Pine, Foley and Lee

[57] ABSTRACT

The invention relates to a process for the synthesis of dibenzofuran by the dehydrocyclization of 2-cyclohexenyl-cyclohexanone at high temperature in the presence of air and a catalyst system selected amongst the known dehydrogenation catalysts.

By the claimed process very high yields of dibenzofuran are achieved.

10 Claims, No Drawings

PROCESS FOR THE SYNTHESIS OF DIBENZOFURAN

The present invention refers to a new process for the synthesis of di-benzofuran, which consists in the oxidative catalytic dehydrocyclization of the 2-cyclohexenyl-cyclohexanone obtainable from cyclohexanone according to methods that are known from the scientific papers.

The dibenzofuran is an important synthetic intermediate in the pharmaceutical industry; in fact some of its derivatives, are claimed to be drugs having anti-inflammatory activity, pain-relieving activity, stress-relieving activity, muscle relaxing activity, vascular dilation activity, sedative activity, or anti-viral activity. Some other derivatives are claimed to be UV stabilizers for olefin polymers, polyacrylates and PVC.

The methods hitherto known for the synthesis of the dibenzofuran consist of the pyrolysis of phenol the catalytic dehydrocyclization of the diphenylether in the presence of $H_2$ on a platinum catalyst supported on active carbon. In the first case the yields obtained are very low, whereas in the second one must resort to expensive raw materials and catalysts. Frequent regenerations of the catalyst itself are necessary, and that causes the process to appear uneconomical.

In a Bayer A.G. patent (Germ. P. 1007772) dibenzofuran is obtained with yields lower than 10%, as an intermediate, starting from 2-cyclohexenyl-cyclohexanone at 420°–480° C in presence of water vapour, on active carbon bed.

It has now been found, and this is the subject of the present invention, that it is possible to obtain very high yields of dibenzofuran by carrying out the dehydrocyclization of the 2-cyclohexenyl-cyclohexanone at high temperature in presence of air and of a catalyst.

The last mentioned catalyst may consist of an ordinary oxidative dehydrogenation catalyst, i.e. oxides or blends of oxides of metals of the III, IV, V, VI and VIII group of the periodic system, e.g. oxides or blends of oxides of cerium, uranium, silicium, titanium, tin, phosphorus, arsenic, antimony, bismuth, vanadium, niobium, tantalum, chromium, molybdenum, tellurium, tungsten, iron, cobalt or nickel.

The catalyst may be used as such or may be supported on the ordinary materials used as supports, such as silica, alumina, diatomite, or silica-alumina. In particular it is preferred to use silica as a support in view of its qualities as a catalyst for oxidative dehydrocyclization, as shown in the Italian Pat. No. 875,126.

The process of the present invention may be carried out in a fixed bed, mobile bed or fluidized bed.

According to a preferred embodiment of the present invention the catalyst consists of a blend of bismuth, molybdenum and vanadium oxides, the preparation of which is reported in Italian Pat. Nos. 690,486 and 769,558.

According to another preferred embodiment of the present invention the catalyst consists of a blend of antimony oxide and of an oxide of a metal selected among the metals belonging to groups III, IV, V and VIII of the periodic system, such as a blend of oxides of antimony and uranium, antimony and tin, antimony and tellurium, antimony and iron, and their more complex blends.

The reaction temperature of the oxidative dehydrocyclization may be between 300° and 700° C and preferably between 400° and 550° C. The reaction pressure may vary within wide limits, i.e., between a few mm Hg and 10 Atm, atmosphere pressure or a little higher is preferred.

Air is the preferred oxidizing agent. It is used in a ratio that may vary from 4 : 1 to 50 : 1 in moles, in respect to the 2-cyclohexenylcyclohexanone; a ratio between 8 : 1 and 30 : 1 is preferred.

Particularly advantageous is the use of an inert diluent which may be chosen among water vapour, nitrogen, argon, carbon dioxide, saturated hydrocarbons or any other substance which does not undergo any change under the reaction conditions.

Particularly preferred is the use of water vapour as a diluent in the molar ratio 5 : 1 to 100 : 1 in respect of 2-cyclohexenylcyclohexanone; a preferential range of ratio is between 10 : 1 and 70 : 1.

In the fixed bed operations the apparent contact time between reagents and catalyst may vary in the range from 0.1 to 10 sec. and preferably from 0.2 to 2.5 sec.

By apparent contact time between reagents and catalyst it is meant the ratio between volume of catalyst bed and flow of the reagents in the gaseous state in the reaction conditions.

The following Examples, exemplify the present invention, and are not meant to be limitations.

It is also reported an example of synthesis of 2-cyclohexenyl-cyclohexanone according to a method deducible from the literature and therefore it is not a subject of the present invention.

In the following examples the terms of conversion, selectivity and yield are used with the following meaning $$\text{Conversion} = \frac{\text{moles of 2-cyclohexenyl-cyclohexanone reacted}}{\text{moles of 2-cyclohexenyl-cyclohexanone fed}} \times 100$$

$$\text{Selectivity} = \frac{\text{moles of dibenzofuran obtained}}{\text{moles of 2-cyclohexenyl-cyclohexanone reacted}} \times 100$$

$$\text{Yield} = \text{conversion} \times \text{selectivity}$$

EXAMPLE 1

Preparation of 2-cyclohexenyl-cyclohexanone

In a 5 liter Pyrex glass flask, equipped with stirrer and loading funnel, topped by a column with Raschig rings and reflux head, cooler and collecting cylinder for the separation of the water-benzene azeotrope, 981.5 g (10 moles) of cyclohexanone were loaded, 1500 cc of benzene and 500 cc of ion exchange resin in acid form of the sulphonic type (Amberlyst 15 of Rohm & Haas).

It was heated for 3 hours with benzene reflux, separating the water by azeotropic distillation, then the reaction mixture after filtering the resin was distilled in order to remove the solvent and subsequently the cyclohexanone was recovered (179.6 g, conversion 81.7%) (boiling point 90° C at 100 mmHg).

The distillation residue contained 1301.2 g (yield 73.1%) of 2-cyclohexenylcyclohexanone together with small quantities of heavier condensation by-products.

The purity of this residue (title in 2-cyclohexenyl-cylohexanone about 90% ) allowed the direct use as feed to the reactor of oxidative dehydrocyclization.

EXAMPLE 2

Oxidative dehydrocyclization on Bi-Mo-V oxides

In a stainless steel reactor, ⅜ inches internal diameter, heated with electrical resistances, 337 g were loaded of a catalyst consisting of a blend of oxides of bismuth, molybdenum, vanadium; prepared according to Example 7 of Italian Pat. No. 769,558.

The composition of the catalyst was 1 $Bi_2O_3$ : 1 $MoO_3$ : 0.6 $V_2O_5$; the catalyst was supported 50% on silica Ludox A/S.

85 cc/hour of 2-cyclohexenylcyclohexanone (purity about 90%), 22 Nl/hour of air and 400 cc/hour of water vapour were fed, for a molar ratio 1 : 20 : 50. The average temperature in the reactor was 450°–500° C. The content time was 0.8 sec.

The average pressure in the reactor was 1 : 1 absolute atmospheres. The reactor effluent was collected by washing in counter current with toluene.

At the end of the test, during 3.5 hours the reaction mixture was distilled at atmospheric pressure in order to remove the toluene, then at 10 mmHg a fraction was collected, boiling p. 130°–135° C which contained 54 g of unreacted 2-cyclohexenylcyclohexanone (conversion 79.8%).

The distillation residue was crystallized from ethanol.

159.2 g of dibenzofuran, yellow crystalline at melting point 85° C were recovered.

The recovery corresponds to a yield of 63%. The selectivity in dibenzofuran was in this test of 79.1%. From the product were absent the cyclization products of 2-cyclohexenylcyclohexanone, not completely converted into aromatics, i.e. tetrahydro and octohydrodibenzofuran.

EXAMPLE 3

Oxidative dehydrocyclization on Fe-Sb oxides

The catalyst for this test was prepared by taking to melting point $Fe(NO_3)_3.6H_2O$, then $Sb_2O_3$ was added in small portions. At the end of the addition of $Sb_2O_3$ heating was applied till the nitrous vapours disappeared.

The catalyst was activated by heating up to 850° C; the end composition was the following : 21.5% w/w of $Fe_2O_3$ — 78.5% w/w of $Sb_2O_3$ corresponding to an atomic ratio Sb/Fe = 2 : 1.

No support was used. In the reactor of Example 2 700 g were loaded of a catalyst prepared in this way, then, at an average reactor temperature of 450°–500° C, 85 cc/hour were fed of 2-cyclohexenylcyclohexanone 90%, 22 Nl/hour of air and 400 cc/hour of water vapour, feed corresponding to molar ratios 2-cyclohexenylcyclohexanone/air/$H_2O$ = 1 : 20 : 50 and a contact time of about 0.8 sec.

The reactor effluent was treated according to the same procedure as Example 2.

In this test there was obtained a conversion of 77.5% of 2-cyclohexenylcyclohexanone with selectivity of 80% to dibenzofuran. The yield in dibenzofuran was then 62%.

We claim:

1. The process of synthesizing dibenzofuran which comprises subjecting 2-cyclohexenylcyclohexanone to oxidative dehydrocyclization at high temperatures in the presence of a dehydrocyclization catalyst which is a member of the group consisting of the oxides and blends of oxides of the metals belonging to groups III, IV, V, VI, and VIII, and an oxidizing agent.

2. A process for the synthesis of dibenzofuran as claimed in claim 1, wherein the reaction is carried out in the presence of a supported catalyst.

3. A process for the synthesis of dibenzofuran as claimed in claim 1, wherein the oxidizing agent is air.

4. A process for the synthesis of dibenzofuran as claimed in claim 3, wherein the air is used in a molar ratio in respect of 2-cyclohexenylcyclohexanone in the range of from 4:1 to 50:1.

5. A process for the synthesis of dibenzofuran as claimed in claim 1, wherein the reaction is carried out in the temperature range between 300° and 700° C.

6. A process for the synthesis of dibenzofuran as claimed in claim 1, wherein the reaction is carried out in the pressure range of from a few mmHg to 10 atmospheres.

7. A process for the synthesis of dibenzofuran as claimed in claim 1, wherein the reaction is carried out in presence of an inert diluent which is a member of the group consisting of water vapour, nitrogen, argon, carbon dioxide and the saturated hydrocarbons.

8. A process for the synthesis of dibenzofuran as claimed in claim 7, wherein the reaction is carried out in the presence of water vapour in a molar ratio in respect of 2-cyclohexenylcyclohexanone in the range of from 5:1 to 100:1.

9. A process for the synthesis of dibenzofuran as claimed in claim 1, wherein the reaction is carried out on a fixed bed.

10. A process for the synthesis of dibenzofuran as claimed in claim 1, wherein the reaction is carried out at an apparent contact time between reagents and catalyst in the range of from 0.1 to 10 sec.

* * * * *